United States Patent [19]
Ellis et al.

[11] Patent Number: 4,816,564
[45] Date of Patent: Mar. 28, 1989

[54] METHOD FOR PRODUCING HEPATITIS B VIRUS PROTEINS IN YEAST

[75] Inventors: Ronald W. Ellis, Overbrook Hills; Arpi Hagopian; Peter J. Kniskern, both of Lansdale, all of Pa.

[73] Assignee: Merck & Co., Inc., Rahway, N.J.

[21] Appl. No.: 824,405

[22] Filed: Jan. 31, 1986

[51] Int. Cl.$^4$ .................. C07K 7/10; C07K 13/00
[52] U.S. Cl. ................................ 530/350; 530/324
[58] Field of Search .............. 530/380, 359, 350, 324

[56] References Cited

U.S. PATENT DOCUMENTS 4,639,371 1/1987 Prince et al. ................. 530/380
4,683,293 7/1987 Craig ............................ 530/359

Primary Examiner—Delbert R. Phillips
Attorney, Agent, or Firm—Donald J. Perrella; Hesna J. Pfeiffer; Julian S. Levitt

[57] ABSTRACT

The entire hepatitis B Virus pre-S antigen gene linked in one contiguous reading frame to the hepatitis B virus surface antigen gene has been expressed in *Saccharomyces cerevisiae*. The expressed protein aggregates into a particulate form which displays the major antigenic sites encoded by both domains, thereby highlighting the utility of yeast as a host for the expression of pre-S domains. This protein is useful in in vitro diagnostic systems and as a vaccine for the treatment and prevention of hepatitis B virus-induced diseases and/or infections.

3 Claims, 5 Drawing Sheets

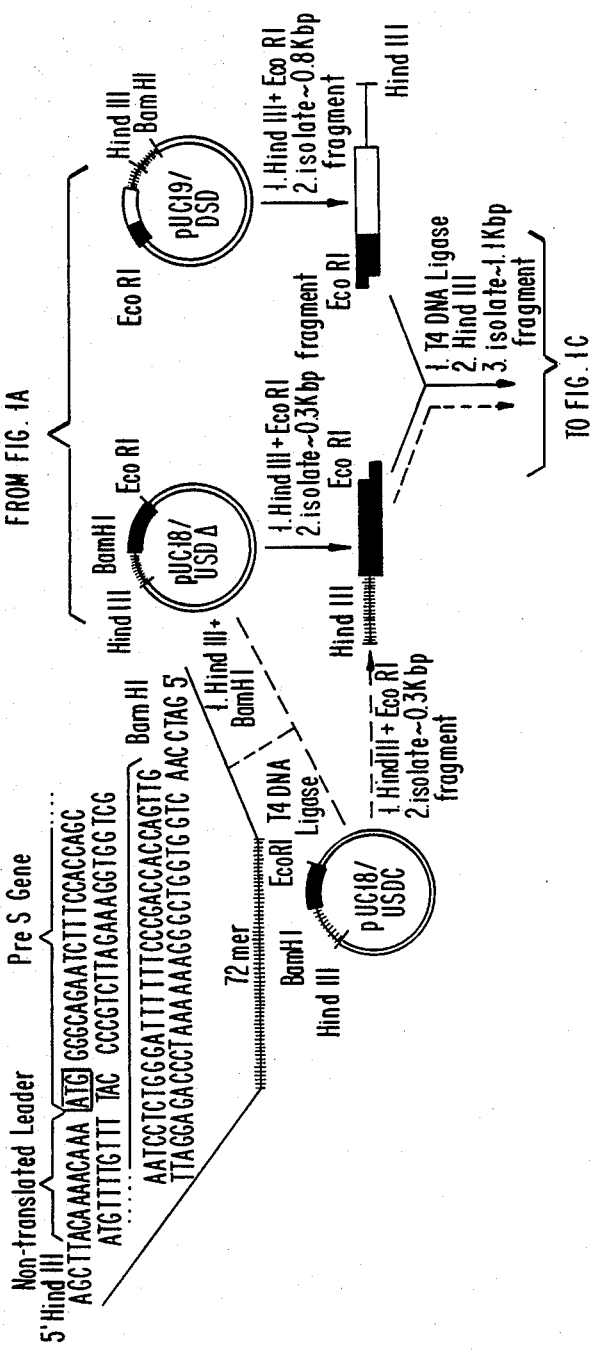

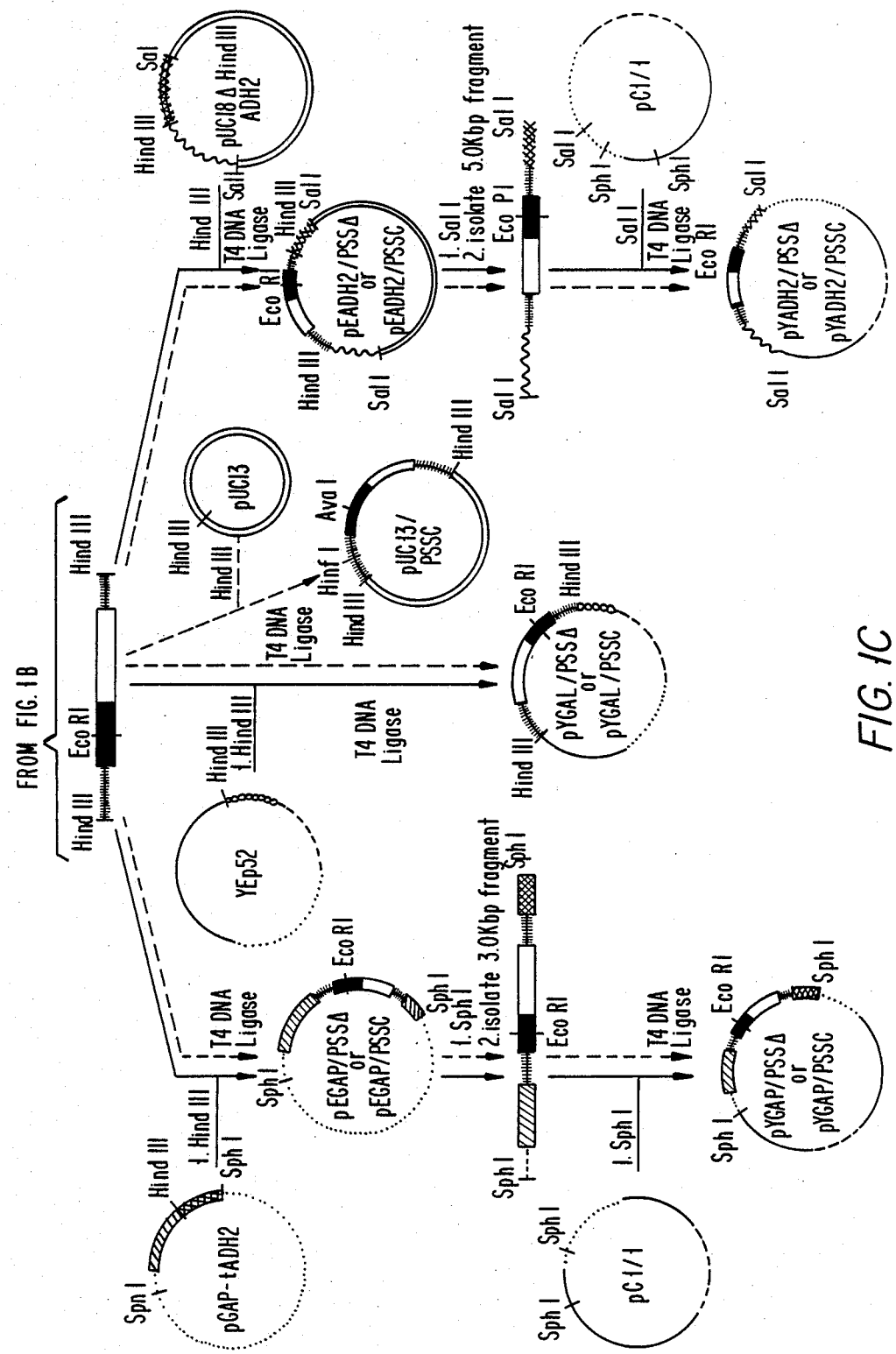
FIG. IC

METHOD FOR PRODUCING HEPATITIS B VIRUS PROTEINS IN YEAST

BACKGROUND OF THE INVENTION

Hepatitis B virus (HBV) is the infectious agent responsible for several varieties of human liver disease. Many individuals who are infected by HBV suffer through an acute phase of disease, which is followed by recovery. However, a large number of individuals fail to clear their infection, thereby becoming chronic carriers of the infection. HBV infection is endemic to many parts of the world, with a high incidence of infection occurring perinatally from chronically infected mothers to their newborns. The number of chronic carriers worldwide has been estimated at over three hundred million. From this pool of carriers, hundreds of thousands die annually from the long-term consequences of chronic hepatitis B (cirrhosis or hepatocellular carcinoma).

The HB virion is composed of two groups of structural proteins, the core proteins and the envelope or surface ("S") proteins. In addition to being the major surface proteins of the virion, i.e., Dane particle, the "S" proteins are the sole constituents of Australia antigen, or 22 nm particles. The "S" proteins are the translational products of a large open reading frame (ORF) encoding 389-400 amino acids, depending upon serotype. This ORF is demarcated into three domains, each of which begins with an ATG codon that is capable of functioning as a translational initiation site in vivo. These domains are referred to as preS-1 (108–119 amino acids), preS-2 (55 amino acids), and S (226 amino acids) in their respective 5'-3' order in the gene. The six protein products derived from this ORF have the following compositions:

(1) gp42 (42,000 dalton glycoprotein)=preS-1/preS-2/S (meaning preS-1, contiguous with preS-2, contiguous with S)

(2) p39 (p=protein)=preS-1/preS-2/S (3) gp36=preS-2/S (two glycosylation sites)

(4) gp33=preS-2/S (one glycosylation site)

(5) gp27=S (one glycosylation site)

(6) p24=S

All six proteins are present to an approximately equimolar extent in the HBV Dane particle. In the 22 nm particle, the 4 smaller proteins are present to an approximately equimolar extent, while gp42 and p39 are present in at most one or a few molecules per particle.

The 22 nm particles, or HB surface antigen (HBsAg) particles, have been purified from the plasma of chronic carriers. In terms of their plasma being particle-positive, these chronic carriers are referred to as HBs+. When these carriers have mounted a sufficient immune response, they can clear the infection and become HBs−. In terms of their formation of antibodies to HBs, these individuals are denoted anti-HBs+. In this way, anti-HBs+ is correlated with recovery from disease. Therefore, the stimulation or formation of anti-HBs+ by HB vaccine has been expected to confer protection against HBV infection.

This hypothesis has been testable experimentally. Outside of man, chimpanzees are the only species which is fully susceptible to HBV infection, as reflected in quantifiable markers such as HBs+, elevated serum levels of liver enzymes, etc. Chimpanzees have been vaccinated with three doses of purified HBsAg particles and then challenged with a large dose of infectious HBV. While mock-vaccinated animals have suffered the signs of acute HBV infection, the HBsAg-vaccinated animals have been protected completely from any signs of infection. Therefore, in this experimental system, HBsAg particles, composed of gp27 and p24 (S domain only), have been sufficient to induce protective immunity. Spurred by these observations, several manufacturers have produced HB vaccines composed of HBsAg particles.

Recent data have suggested that the preS-1 and preS-2 domains may play an important role in immunity to HBV infections. Both antibodies to preS-1 (elicited by immunization with a peptide consisting of amino acid residues 10–32 of preS-1) as well as antibodies to preS-2 (elicited by immunization with a peptide consisting of amino acid residues 1–26 of preS-2) are capable of blocking the binding of HBV to human hepatoma cells in vitro; anti-HBs (sera from patients vaccinated with HBsAg lacking preS-1 or preS-2) is incapable of mediating this blocking event. If this in vitro event mimics in vivo infection, then pre-S (i.e., preS-1 and preS-2 in toto linked together) domains may represent the HBV binding site to its liver cell receptor, and anti-pre-S may block HBV attachment and initiation of infection. In addition, it has been found that anti-pre-S rises in titer during the recovery phase from acute HBV infection, indicating a role for these antibodies in recovery. Finally, it has been shown that vaccination of chimpanzees with a 108 amino acid pre-S polypeptide (residues 27–119 of preS-1 contiguous with 1–16 of preS-2) was capable of mediating some measure of protection against HBV challenge. In sum, these experimental observations have suggested that the pre-S domains are a useful addition to present HB vaccines.

In order to expand the available supply of HB vaccines, manufacturers have turned to recombinant DNA technology to mediate the expression of "S" proteins. Among microbial systems, *Escherichia coli* and *Saccharomyces cerevisiae* have been used most commonly for the expression of many recombinant-derived proteins. Numerous attempts to express immunologically active HBsAg particles in *E. coli* have been unsuccessful. However, *S. cerevisiae* has shown great versatility in its ability to express immunologically active HBsAg particles. These particles, when formulated into a vaccine, have proven capable of fully protecting chimpanzees against challenge with live HBV. Furthermore, yeast-derived HBsAg has been as effective immunologically in human clinical trials as plasma-derived HBsAg. Therefore, the utility of *S. cerevisiae* as a host species for directing synthesis of recombinant HBsAg is established firmly. In light of this, it would be desirable to express the entire pre-S domain linked to the S domain in an immunogenic particle.

In a variety of recombinant microbial expression systems, the synthesis of many different polypeptides has been shown to be deleterious to the host cell. As a consequence, there is selective pressure against the expression of such polypeptides, such that the only cells which accumulate in a scale-up of such a recombinant culture are those which have ceased to express the foreign polypeptide or express so little of the foreign polypeptide that the culture becomes an uneconomical source of that polypeptide. In some cases, the deleterious effect is so strong that when expression is driven by a strong constitutive promoter, newly transformed cells fail to propagate and form colonies on selective plates.

These deleterious effects can be overcome by using an inducible promoter to direct the synthesis of such polypeptides. A number of inducible genes exist in *S. cerevisiae*. Three well-characterized inducible systems are the galactose (GAL) utilization genes, the alcohol dehydrogenase 2 (ADH2) gene, and the alpha mating factor gene.

*S. cerevisiae* has 3 genes which encode the enzymes responsible for the utilization of galactose as a carbon source for growth. The GAL1, GAL7 and GAL10 genes respectively encode galactokinase, α-D-galactose-1-phosphate uridyltransferase and uridine diphosphogalactose-4-epimerase. In the absence of galactose, very little expression of these enzymes is detected. If cells are grown on glucose and then galactose is added to the culture, these three enzymes are induced coordinately, by at least 1,000-fold, at the level of RNA transcription. The GAL1 and GAL10 genes have been molecularly cloned and sequenced. The regulatory and promoter sequences to the 5' sides of the respective coding regions have been placed adjacent to the coding regions of the lacZ gene. These experiments have defined those promoter and regulatory sequences which are necessary and sufficient for galactose induction.

*S. cerevisiae* also has 3 genes, each of which encodes an isozyme of ADH. One of these enzymes, ADHII, is responsible for the ability of *S. cerevisiae* to utilize ethanol as a carbon source during oxidative growth. Expression of the ADH2 gene, which encodes the ADHII isozyme, is catabolite-repressed by glucose, such that there is virtually no transcription of the ADH2 gene during fermentative growth in the presence of glucose levels of >0.1% (w/v). Upon glucose depletion and in the presence of non-repressing carbon sources, transcription of the ADH2 gene is induced 100- to 1000-fold. This gene has been molecularly cloned and sequenced, and those regulatory and promoter sequences which are necessary and sufficient for derepression of transcription have been defined.

Alpha mating factor is a sex pheromone of *S. cerevisiae* which is required for mating between MATα and MATa cells. This tridecapeptide is expressed as a pre-propheromone which is directed into the rough endoplasmic reticulum, glycosylated and proteolytically processed to its final mature form which is secreted from cells. This biochemical pathway has been exploited as an expression strategy for foreign polypeptides. The alpha mating factor gene has been molecularly cloned and its promoter with pre-proleader sequence has been utilized to express and secrete a variety of polypeptides. As expected by their traversal of the rough endoplasmic reticulum and Golgi apparatus, foreign proteins can undergo both N- and O-linked glycosylation events. The alpha mating factor promoter is active only in cells which are phenotypically α. There are 4 genetic loci in *S. cerevisiae*, known as SIR, which synthesize proteins required for the repression of other normally silent copies of a and α information. Temperature-sensitive (ts) lesions which interfere with this repression event exist in the gene product of at least one of these loci. In this mutant, growth at 35° C. abrogates repression, resulting in cells phenotypically a/α in which the alpha mating factor promoter is inactive. Upon temperature shift to 23° C., the cells phenotypically revert to α such that the promoter becomes active. The use of strains with a ts SIR lesion has been demonstrated for the controlled expression of several foreign polypeptides.

OBJECTS OF THE INVENTION

It is an object of the present invention to provide expression vectors and processes for the expression of the preS-1 and preS-2 domains operably linked to the S domain in yeast as an immunogenic particle. Another object is to provide vectors and processes for the expression of the preS-1 and preS-2 domains in yeast. Another object is to specify conditions for the scale-up of the growth of recombinant host cells transformed by such vectors, such that maximal yields of preS-containing polypeptides can be attained in large volumes and concentrations for the purification of such polypeptides. These and other objects of the present invention will be apparent from the following description.

SUMMARY OF THE INVENTION

The entire hepatitis B virus pre-S antigen gene linked in one contiguous reading frame to the hepatitis B virus surface antigen gene has been expressed in *Saccharomyces cerevisiae*. The expressed protein aggregates into a particulate form which displays the major antigenic sites encoded by both domains, thereby highlighting the utility of yeast as a host for the expression of the pre-S domain. This protein is useful in in vitro diagnostic systems and as a vaccine for the treatment and prevention of hepatitis B virus-induced diseases and/or infections.

BRIEF DESCRIPTION OF THE DRAWINGS

FIGS. 1A, 1B and 1C are schematic diagrams illustrating the construction of plasmids pYGAP/PSSΔ, pYGAP/PSSC, pYGAL/PSSΔ, pYGAL/PSSC, pYADH2/PSSΔ, pYADH2/PSSC, and pUC13/PSSC.

DETAILED DESCRIPTION OF THE INVENTION

Figure 1A:
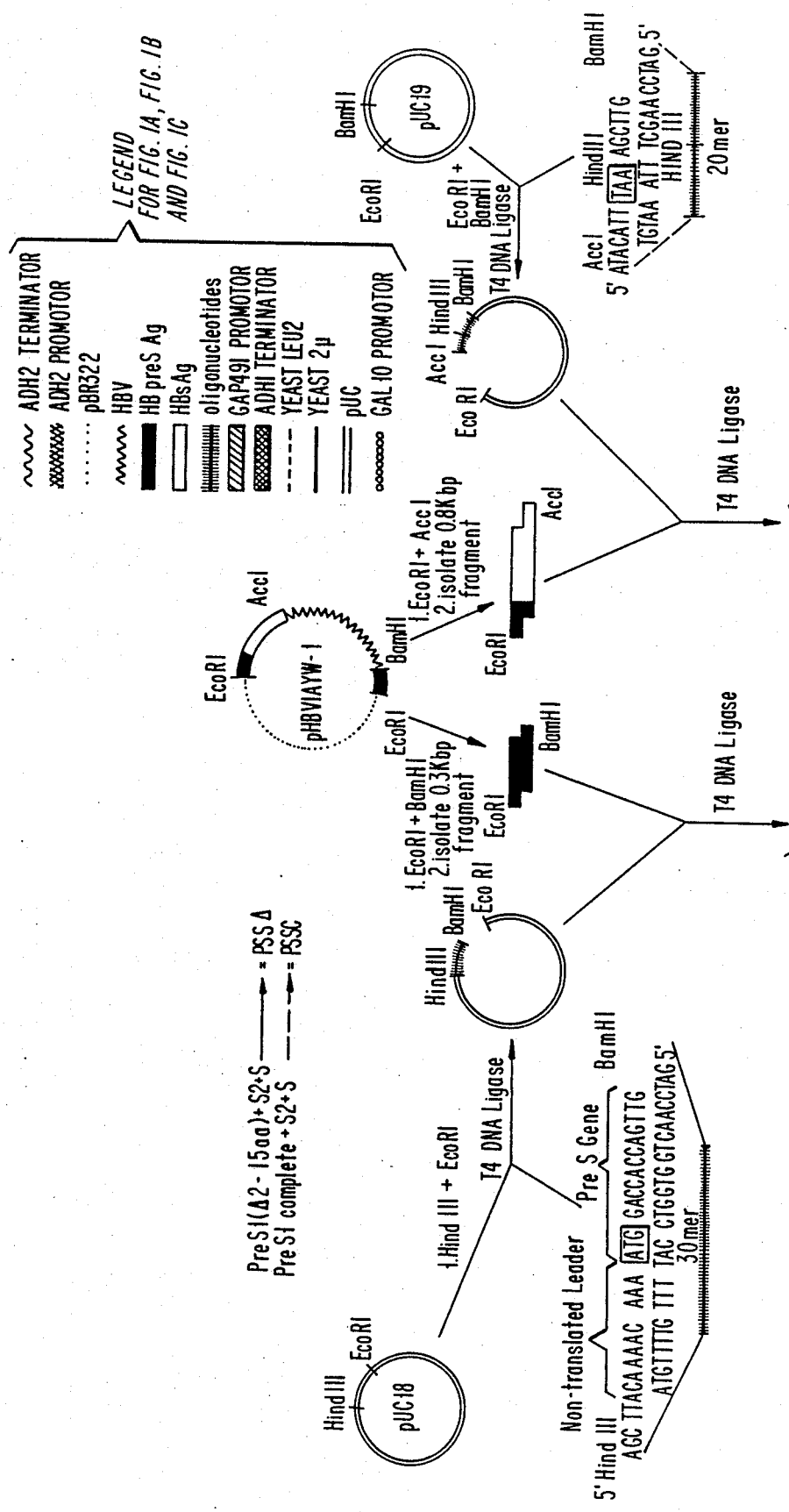

The present invention is directed to a method for the expression in yeast species of the pre-S domain (or portions thereof) linked to the S domain as a contiguous polypeptide or of the pre-S domain per se (or portions thereof). More specifically, it is directed to the use of a galactose-inducible promoter, a glucose-repressible promoter, and a temperature-inducible promoter to direct expression of these domains in species of the genus Saccharomyces, in order to overcome the toxic effect of the pre-S domain upon the host when expression of this domain is directed by a strong constitutive promoter. In addition, it is directed to conditions for the scale-up to large volumes of recombinant cells expressing pre-S-containing polypeptides in a particulate form. It will be obvious to those skilled in the art that other promoters whose activity can be regulated physiologically (i.e., inducible) can be utilized to direct the expression of pre-S-containing polypeptides in yeast species in order to overcome the above-mentioned toxic effect of the pre-S domain.

Dane particles are utilized as the source of HBV nucleic acid for the isolation of the preS-1/preS-2/S ORF. The endogenous polymerase reaction is employed in order to produce covalently closed circular double-stranded DNA of the HBV genome from the nicked and gapped form that resides natively in the HB virion. The repaired DNA is isolated and digested to completion with EcoRI. The *E. coli* cloning vector pBR322 also is digested with EcoRI, ligated to the HBV DNA and used to transform *E. coli*. Recombinant plasmids are selected, these containing the HBV genome in a circularly permuted form in which the EcoRI site divides the complete preS-1/preS-2/S coding region into a 5' domain of 0.4 kilobase pairs (kbp) and a 3' domain of 0.8 kbp. These two domains are subcloned for the eventual reassembly of the entire gene. For the 3' domain, pUC19 is digested with EcoRI and BamHI, then ligated to a synthetic oligonucleotide which consists of the final 5 nucleotides of the coding region, the stop codon, a HindIII site, and a BamHI end. The 3' portion of the preS-1/preS-2/S gene, consisting of a 0.8 kbp EcoRI-AccI fragment, is cloned into this vector. The 5' portion, consisting of a 0.3 kbp BamHI-EcoRI fragment, is subcloned into pUC18 in either of two ways, depending upon whether (1) the complete ORF is to be expressed or (2) the putative hydrophobic signal sequence (amino acids 2–15) is to be eliminated. For the first strategy, pUC18 is digested with HindIII and EcoRI and ligated to a 72 bp synthetic oligonucleotide which reconstitutes the complete ORF from the BamHI site upstream, through the distal ATG and a 10 bp non-translated leader sequence, to a HindIII compatible terminus. For the second strategy, there is ligated a 30 bp oligonucleotide which performs an identical function but which eliminates the coding region for amino acids 2–15. The 0.3 kbp BamHI-EcoRI fragment of the 5' domain then is ligated into either of these oligonucleotide-linked cloning vectors. The 5' pUC18 and 3' pUC19 clones are amplified by growth in *E. coli*, and the coding regions are digested from the isolated plasmids as HindIII-EcoRI fragments. The 5' and 3' fragments are ligated, digested with HindIII, and the complete ORF with HindIII termini is cloned into pUC13 which had been digested previously with HindIII. The complete ORF as a HindIII fragment is purified by preparative agarose gel electrophoresis for cloning into the GAPDH, ADH2 or GAL10 promoter expression systems.

The PBR322 plasmid containing the GAPDH expression cassette possesses a unique HindIII site between the GAPDH promoter and the ADH1 transcriptional terminator into which the complete ORF from pUC13 described above is inserted in the appropriate orientation. This 3.0 kbp expression cassette then is removed by SphI digestion and ligated into the shuttle vector pC1/1 to replace the small SphI fragment. Vectors constructed in this manner are used to transform *S. cerevisiae* strain 2150-2-3; however, plating out the transformation mixture onto selective plates results in no stable colony formation. The suspected toxicity of the expressed product is confirmed by the removal of the majority of the PreS1-PreS-2/S coding region and creation of a frameshift mutation by BamHI digestion and religation of the plasmid; DNA prepared in this way efficiently transforms yeast cells.

The YEp52 *E. coli/S. cerevisiae* shuttle vector drives expression of foreign genes inserted at a unique HindIII site from the galactose-inducible GAL10 promoter. The PreS-1/PreS-2/S ORF (with HindIII termini) described above is ligated into the HindIII site of the vector. This recombinant plasmid is introduced to *S. cerevisiae* strain BY-19 and transformed clones are selected. Cells are grown in synthetic selective medium containing glycerol-lactic acid. Subsequently, galactose is added to the cultures to induce expression. Lysates are prepared, resolved by sodium dodecyl sulfate-plyacrylamide gel electrophoresis (SDS-PAGE) and Western blotted to nitrocellulose. A p39 product is found to be specific to preS-1/preS-2/S by virtue of its presence only in induced transformants and its reactivity with convalescent human HB sera. Furthermore, lysates of transformants, but not wild-type *S. cerevisiae*, are positive for HBsAg by radioimmunoassay and are positive for pre-S by virtue of binding to polymerized human albumin, a binding which has been shown to be specific to the pre-S region. An immune-affinity column, bound with goat antibodies which recognize the particulate form of HBsAg, has been utilized to purify preS-1/preS-2/S from transformed *S. cerevisiae*. The eluted product is positive for HBsAg by radioimmunoassay, is positive for pre-S by polymerized human albumin binding, and is of particulate form in electron microscopy. These data demonstrate that the entire preS-1/preS-2/S protein is expressed in *S. cerevisiae* as a p39 protein present in particulate form. Such a particulate form which contains both HBs and pre-S antigens is effective as a HB vaccine and diagnostic reagent.

The pADH2Δ67(-1) *E. coli* cloning vector contains sequences which are capable in *S. cerevisiae* of driving expression of foreign genes inserted at a unique HindIII site from the ADH2 (glucose-repressible) promoter. pADH2Δ67(-1) is digested with BamHI and EcoRI, made flush-ended with the Klenow fragment of DNA polymerase I, and the 4.9 kbp fragment containing the ADH2 promoter and terminator purified by preparative agarose gel electrophoresis. pUC7 is digested with PstI, made flush-ended with T4 DNA polymerase, and ligated to the 4.9 kbp fragment. The resulting plasmid is digested with SalI, and the 4.9 kbp fragment is purified by preparative agarose gel electrophoresis. pUC18 is digested with HindIII, made flush-ended with the Klenow fragment of DNA polymerase I, and self-ligated. The resulting plasmid is digested with SalI and ligated to the 4.9 kbp SalI fragment. The 1.2 kbp PreS-1/PreS-2/S ORF (with HindIII termini) described above is ligated into the HindIII site of this vector. The resulting plasmid is digested with SalI, and the 6.1 kbp fragment is ligated into the SalI site of the shuttle vector pC1/1. Plasmid pC1/1 is a derivative of pJDB219 in which the region corresponding to bacterial plasmid pMB9 in pJDB219 was replaced by pBR322. This recombinant plasmid is introduced into *S. cerevisiae*, and transformed clones are selected. Cells are grown in synthetic selective medium containing 0.3% (w/v) glucose. Forty-eight hours later, following glucose depletion, lysates are prepared, resolved by SDS-PAGE and Western blotted to nitrocellulose. A p39 product is found to be specific to preS-1/preS-2/S by virtue of its presence only in transformants and its reactivity with convalescent human HB sera. Furthermore, lysates of transformants, but not wild-type *S. cerevisiae*, are positive for HBsAg by radioimmunoassay and are positive for pre-S by binding to polymerized human albumin. An immune-affinity column, bound with goat antibodies which recognize the particulate form of HBsAg, has been utilized to purify preS-1/preS-2/S from transformed *S. cerevisiae*. The eluted product is positive for HBsAg by radioimmunoassay, is positive for pre-S by polymerized human albumin binding, and is of particulate form in electron microscopy.

The alpha mating factor gene MFα1 has been cloned onto a plasmid vector from *S. cerevisiae* genomic DNA. The resulting plasmid pKH2 is digested with EcoRI and the 1.7 kbp fragment bearing the alpha mating factor gene is purified by preparative agarose gel electrophoresis. Plasmid pRJ148 (a modified pBR322 lacking the HindIII site) is digested with EcoRI and ligated with the 1.7 kbp fragment to yield the plasmid pRJ159. This DNA is digested with HindIII and self-ligated to form plasmid pRJ167, which now has a unique HindIII site. Plasmid pRJ167 is digested with HindIII and modified by the insertion of a synthetic oligonucleotide adaptor to yield a new plasmid (pRJ178) containing a unique HindIII site which is to the 3' side of the promoter and pre-pro-leader and to the 5' side of the translational termination signals in all three reading frames. The HindIII site is converted to a BamHI site by digestion with HindIII, flush-ending with the Klenow fragment of DNA polymerase I, addition of BamHI linkers and self-ligation to form plasmid pJC193. This plasmid is digested with EcoRI, flush-ended with the Klenow fragment of DNA polymerase I, modified by the addition of BclI linkers, digested with BclI, and the 1.5 kbp fragment bearing the alpha mating factor gene isolated by preparative gel electrophoresis. This resulting BclI fragment is treated with calf intestine alkaline phosphatase and then is inserted into the unique BamHI site of pC1/1, destroying the original BamHI site in the process (plasmid pJC194). This DNA is digested with BamHI and self-ligated to remove excess BamHI linkers, resulting in the new alpha mating factor expression plasmid pJC197. The preS-1/preS-2/S ORF in pUC13 described above is digested with HinfI and AvaI, and the 0.5 kbp ORF is purified by preparative agarose gel electrophoresis. pUC18 is digested with SalI and BamHI, then ligated to 2 synthetic oligonucleotides. The 5' oligonucleotide consists of a SalI terminus, a HindIII site, nucleotides encoding a KEX2 cleavage site, nucleotides encoding amino acids 2 and 3 of preS-1, and a HinfI terminus. The 3' oligonucleotide contains an AvaI site, nucleotides encoding the final 8 amino acids of preS-2, the stop codon, a HindIII site, and a BamHI terminus. The 0.5 kbp ORF is cloned into this oligonucleotide-linkered pUC18 vector. The resulting vector is digested with HindIII and blunt-ended with the Klenow fragment of DNA polymerase I. The resulting modified 0.5 kbp preS-1/preS-2 ORF is purified by preparative agarose gel electrophoresis and cloned into pJC197 which had been digested with BamHI and blunt-ended with the Klenow fragment of DNA polymerase I resulting in the preS ORF being operably linked to the pre-pro-leader sequence of alpha mating factor.

The alpha mating factor promoter is active only in cells which are phenotypically α. There are 4 loci in *S. cerevisiae*, known as SIR, which synthesize proteins required for the repression of other normally silent copies of a and α information. Strain JRY188 cells (MATα, sir3-8, leu2-3, leu2-112, trp1, ura3-52, his4) contain a ts lesion in the SIR3 gene product. As a result, JRY188 cells grown at 35° C. are phenotypically a/α and the alpha mating factor promoter is not active; on the other hand, cells grown at 23° C. are phenotypically α and thus capable of inducing an expression directed by the alpha mating factor promoter. The recombinant preS-1/preS-2-containing alpha mating factor plasmid is used to transform *S. cerevisiae* strain JRY188 and transformed clones are selected. Cells are grown in synthetic selective (leu−) medium at 35° C.; subsequently, cells at $A^{600}=0.5$ are grown in the same medium at 23° C. Lysates are prepared, resolved by SDS-PAGE, and Western blotted to nitrocellulose. A p21 product is found to be specific to preS-1/preS-2 by virtue of its presence only in transformants and its reactivity with convalescent human HB sera.

The inability of the vector which directs preS-1/preS-2/S expression from the constitutive GAPDH promoter to stably transform *S. cerevisiae* highlights the negative physiological effect of constitutive and high-level pre-S expression upon *S. cerevisiae;* the plasmid pHBS56-GAP347/33, which directs S polypeptide expression from this same promoter, efficiently transforms *S. cerevisiae* and such transformed *S. cerevisiae* grow efficiently to production scale. This observation highlights the utility of a shuttle vector which utilizes an inducible, derepressible, or less active constitutive promoter to direct the expression of preS-containing polypeptides in *S. cerevisiae*. In particular, this highlights the utility of the expression vector which utilizes the GAL10 promoter to direct the expression of preS-1/preS-2/S in *S. cerevisiae*. It is obvious to those skilled in the art that the regulatable GAL10 promoter, or GAL1, GAL2, GAL7 or MEL1 promoters which function in an indistinguishable manner, enable the growth of a recombinant *S. cerevisiae* culture to be scaled up to a production-scale volume before synthesis of the recombinant protein is initiated, such that negative effects on the host cell are minimized. Moreover, it is obvious to those skilled in the art that an expression vector containing another regulatable promoter, including but not limited to ADH2 and alpha mating factor, physiologically inducible or derepressible by other means, can be utilized to direct expression of pre-S-containing polypeptides. Furthermore, it is obvious to those skilled in the art that a constitutive promoter less potent than GAPDH, including but not limited to CYC1, drives expression of pre-S-containing polypeptides to a lower percentage of cell protein, such that the negative physiological effects of overexpression would be obviated. It is obvious to those skilled in the art that a suitable assay system, e.g., Western blot or radioimmunoassay, should be utilized in order to assay expression of pre-S-containing polypeptides in this system so that the time of harvesting of the culture for attaining a maximal yield can be optimized.

The genus Saccharomyces is composed of a variety of species. Most commonly used is *Saccharomyces cerevisiae*, or baker's yeast, as a host for the recombinant DNA-mediated expression of a variety of foreign polypeptides. However, the distinctions among other species of the genus Saccharomyces are not always well-defined. Many of these species are capable of interbreeding with *S. cerevisiae* and are likely to possess regulatable promoters which are analogous or identical to promoters in *S. cerevisiae*, including but not limited to GAL10, ADH2, and/or alpha mating factor promoters. Therefore, it will be obvious to those skilled in the art that, for the expression of pre-S-containing polypeptides, the selection of a host strain extends to other species of the genus Saccharomyces, including but not limited to *carlsbergensis, uvarum, rouxii, montanus, kluyveri, elongisporus, norbensis, oviformis,* and *diastaticus*.

Several yeast genera, such as Hansenula, Candida, Torulopsis, and Pichia, have been shown to contain similar metabolic pathways for the utilization of methanol as a sole carbon source for growth. The gene for alcohol oxidase, an enzyme which participates in this metabolic pathway, has been isolated from *Pichia pastoris*. The *P. pastoris* alcohol oxidase promoter has been isolated and shown to be susceptible to methanol induction of expression. Such an inducible promoter is useful for the expression of polypeptides which are negatively selected in yeast. In particular, this promoter has been shown to be active on a plasmid for the inducible expression of the S domain in *P. pastoris* in particulate form. This observation highlights the ability of other yeast genera to function as hosts for the recombinant DNA-mediated expression of S polypeptides in immunologically active form. Therefore, it will be obvious to those skilled in the art that, for the expression of pre-S-containing polypeptides, the selection of a host strain extends to species from other genera of yeast from the Families Saccharomycetaceae and Cryptococcaceae, including, but not limited to Pichia, Candida, Hansenula, Torulopsis, Kluyveromyces, and Saccharomycopsis.

In recent years, there have been notable successes reported in the expression of recombinant proteins in cells of eukaryotes higher than yeast, in particular in mammalian cell lines and in insect cells transfected with baculovirus expression vectors. Successful expression as an immunogenic particle of both the S domain per se as well as the preS-2 domain linked to the S domain has been achieved. Therefore, it will be obvious to those skilled in the art that the concept of expressing the complete preS-1/preS-2/S domains in yeast as an immunogenic particle readily extends to expression of these linked domains in cells of higher eukaryotes, including but not limited to mammalian cell lines such as vero, GH3, Ltk− and CHO.

The following examples illustrate the present invention without, however, limiting the same thereto. The disclosure of each reference mentioned in the following examples is hereby incorporated by reference.

EXAMPLE 1

Cloning the preS-1/preS-2/S Gene

Dane particles (subtype ayw) were purified from the plasma of infected individuals by established techniques [Landers et al., J. Virology 23: 368 (1977)]. The HBV genomic DNA resides in a nicked, gapped form in the virion [Hruska et al., J. Virology 21: 666 (1977)]. In order to prepare this DNA for molecular cloning, the endogenous polymerase reaction was employed to produce covalent closed circular double-stranded DNA [Landers et al., J. Virology 23: 368 (1977)]. The DNA was deproteinized by incubation in buffer containing sodium dodecyl sulfate and, Proteinase K followed by extraction with phenol: chloroform:isoamyl alcohol (25:24:1) and concentration by ethanol precipitation. This purified DNA was digested to completion with EcoRI. The *E. coli* cloning vector pBR322 also was digested with EcoRI, ligated to the digested HBV DNA and used to transform *E. coli*. Recombinant plasmids were isolated which contain the HBV genome in a circularly permuted orientation about the unique EcoRI site (pHBV/AYW-1, FIG. 1), which divides the complete preS-1/preS-2/S coding region into a 5′ domain of 0.4 kbp and a 3′ domain of 0.8 kbp [Galibert et al., Nature 281: 646 (1979)]. These two domains were subcloned for the eventual reassembly of the entire gene. pUC19 was digested with EcoRI and BamHI, then ligated to a synthetic oligonucleotide which consists of the final 5 nucleotides of the coding region, the stop codon, a HindIII site, and a BamHI end. The structure of this oligonucleotide is

ATACATTTAAAGCTTG
TGTAAATTTCGAACCTAG

The 3′ portion of the preS-1/preS-2/S gene, consisting of a 0.8 kbp EcoRI-AccI fragment was cloned into this vector (pUC19/DSD, FIG. 1).

The 5′ portion was subcloned into pUC18 in either of two ways, depending upon whether the complete ORF was to be expressed or the putative hydrophobic signal sequence (amino acids 2–15) was to be eliminated. For the first strategy, pUC18 was digested with HindIII and EcoRI and ligated to 72 bp synthetic oligonucleotide which reconstitutes the complete ORF from the BamHI site upstream to the distal ATG through a 10 bp non-translated leader sequence to a HindIII compatible terminus. The structure of this oligonucleotide is:

AGCTTACAAAACAAAATGGG-
GCAGAATCTTTCCACCAGCAATCCTCTG-
GGATTTTT*
ATGTTTTGTTTTACCCCGTCT-
TAGAAAGGTGGTCGTTAGGAGACC-
CTAAAAA*
TCCCGACCACCAGTTG
AGGGCTGGTGGTCAACCTAG (*the natural sequence contains C rather than T; The above change destroys the HinfI site without changing the encoded amino acid.) For the second strategy, there was ligated a 30 bp oligonucleotide which performed an identical function as the 72 bp oligonucleotide but which eliminated the coding region for amino acids 2–15. The structure of this oligonucleotide is

AGCTTACAAAACAAAATGGACCAC-
CAGTTG
ATGTTTTGTTTTACCTGGTGGTCAACC-
TAG

The 0.4 kbp BamHI-EcoRI fragment of the 5′ domain then was ligated into either of these oligonucleotide-linked cloning vectors (pUC18/USDΔ, pUC18/USDC, FIG. 1). The 5′ pUC18 and 3′ pUC19 clones were amplified by growth in *E. coli*, and the coding regions were digested from the isolated plasmids as HindIII-EcoRI fragments. These fragments were ligated, digested with HindIII, and the complete ORF with HindIII termini was cloned into pUC13 which had been digested with HindIII (pUC13/PSSΔ, pUC13/PSSC: FIG. 1). The complete ORF from this vector was purified by preparative agarose gel electrophoresis for cloning into the GAPDH or GAL10 promoter (YEp52) or ADH-2 promoter expression systems, as described in Examples 2, 3 and 4.

EXAMPLE 2

Use of the GAPDH promoter to direct expression of preS-1/preS-2/S in *S. cerevisiae*

The PBR322 plasmid containing the GAPDH expression cassette [Holland and Holland, J. Biol. Chem. 255: 2596 (1980)] has a unique HindIII cloning site into which the 1.1 kbp preS-1/preS-2/S ORF with HindIII termini (described in Example 1) was cloned (pEGAP/PSSΔ, pEGAP/PSSC, FIG. 1). The expression cassettes (containing the HBV genes) were removed from the PBR322 plasmid by SphI digestion and preparative agarose gel electrophoresis. The expression cassettes then were cloned into the shuttle vector pC1/1 [Beggs, Nature 275: 104 (1978); Rosenberg et al., Nature 312: 77 (1984)] which had been digested previously with SphI (pYGAP/PSSΔ, pYGAP/PSSC, FIG. 1). The pC1/1 plasmid containing the expression cassettes was used to transform *S. cerevisiae* strain 2150-2-3; however, few stable recombinant yeast clones could be recovered from selective plates following plating out of the transformation mixture. The suspected toxicity of the pre-S containing product for *S. cerevisiae* was confirmed by removal of the pre-S1/preS-2/S coding region and creation of a frameshift mutation by BamHI digestion and religation of the plasmid; DNA prepared in this manner efficiently transformed yeast.

EXAMPLE 3

Use of the GAL10 promoter to direct expression of preS-1/preS-2/S in *S. cerevisiae*

The YEp52 *E. coli/S. cerevisiae* shuttle vector drives expression of foreign genes inserted at a unique HindIII site from the galactose-inducible GAL10 promoter [Broach et al., In *Experimental Manipulation of Gene Expression*, p83, Academic Press (1983)]. In addition, this vector contains partial 2μ circle sequences (ori and one inverted repeat) for propagation in *S. cerevisiae*, LEU2 for selection in *S. cerevisiae*, and the ori and bla sequences for amplification and selection, respectively, in *E. coli*. The 1.1 kbp preS-1/preS-2/S ORF with HindIII termini (described in Example 1) was cloned into the unique HindIII site (pYGAL/PSSΔ, pY-GAL/PSSC, FIG. 1), and the resultant plasmid was used to transform *S. cerevisiae* strain BY-19. Recombinant clones were isolated and examined for expression of the preS-1/preS-2/S polypeptide. Clones were grown in synthetic selective (leu−) glycerol-lactic acid medium [0.67% (w/v) yeast nitrogen base without amino acids, 0.004% adenine, 0.004% uracil, 1% succinate, 0.005% tyrosine, 0.002% arginine, 0.006% isoleucine, 0.004% lysine, 0.001% methionine, 0.006% phenylalanine, 0.006% threonine, 0.004% tryptophan, 0.001% histidine, 0.6% sodium hydroxide, 2% (v/v) lactic acid, 3% (v/v) glycerol]. Production of the gene product was induced by the addition of galactose to 2% (w/v) after the yeast had grown to an $A^{600}=0.3$. Expression of the desired antigen was verified by the detection of HBsAg by Ausria ® (Abbott) reactivity, polymerized human albumin binding activity [Machida et al., Gastroenterology 86: 910 (1984)] and the presence of p39 in Western blots which were developed using convalescent human serum and radiolabelled *Staphylococcus aureus* protein A. These recombinant clones served as seed cultures for the large-scale fermentation and isolation described in Example 6.

EXAMPLE 4

Use of the ADH2 promoter to direct expression of preS-1/preS-2/S in *S. cerevisiae*

The pADH2Δ67(-1) *E. coli* cloning vector contains sequences which are capable in *S. cerevisiae* of driving expression of foreign genes inserted at a unique HindIII site from the ADH2 derepressible promoter [Russell et al., J. Biol. Chem. 258: 2674 (1983); E. T. Young, submitted for publication]. The unique HindIII site is positioned between nucleotide -1 of the 5′ nontranslated flanking sequences and the transcriptional terminator of the ADH2 gene. pADH2Δ67(-1) was digested with BamHI and EcoRI, made flush-ended with the Klenow fragment of DNA polymerase I, and the 4.9 kbp fragment containing the ADH2 promoter and terminator was purified by preparative agarose gel electrophoresis. pUC7 was digested with PstI, made flush-ended with T4 DNA polymerase, and ligated to the 4.9 kbp ADH2 fragment. The resulting plasmid was digested with SalI, and the 4.9 kbp fragment was purified by preparative agarose gel electrophoresis. pUC18 was digested with HindIII, made flush-ended with the Klenow fragment of DNA polymerase I, and self-ligated. The resulting plasmid was digested with SalI and ligated to the 4.9 kbp SalI fragment, creating the vector pUC18ΔHindIII-ADH2 (FIG. 1). The two different 1.1 kbp preS-1/preS-2/S ORFs with HindIII termini (described in Example 1) were ligated into the HindIII site of this vector. The resulting plasmid (pEADH2/PSSΔ, pEADH2/PSSC, FIG. 1) was digested with SalI, and the 6.1 kbp fragment was ligated into the SalI site of pC1/1 creating the plasmids pYADH2/PSSΔ, pYADH2/PSSC (FIG. 1). These recombinant plasmids were used to transform *S. cerevisiae* strain 2150-2-3. Recombinant clones were isolated and examined for expression of the preS-1/preS-2/S polypeptide. Clones were grown in synthetic selective (leu−) medium containing 0.3% (w/v) glucose. Cells were grown for 48 hours at 30° C. to an $A^{600}=1.5$, during which time glucose depletion had derepressed the ADH2 promoter. Alternatively the clones were grown in synthetic selective (leu−) medium containing 2% glucose as a carbon source. Cells were grown for 24 hours at 30° C. to an $A^{600}$ of either 0.1 or 1.0, at which time larger flasks or fermenters containing complex medium with 1.6% glycose as a carbon source were inoculated (inoculum size=10% vol/vol). Cells were grown for an additional 45 hours as described above to an $A^{600}=12.0-14.0$, during which time glucose depletion had derepressed the ADH2 promoter. Expression of the desired antigen was verified by the detection of HBsAg by AUSRIA ® (Abbott) reactivity, polymerized human albumin binding activity, and the presence of p39 in Western blots which were developed using convalescent human serum and radiolabelled *Staphylococcus aureus* protein A. A selected recombinant clone served as a seed culture for the scale-up fermentation and isolation described in Example 7.

EXAMPLE 5

Use of the alpha mating factor promoter and pre-pro-leader to direct expression of preS-1/preS-2 in *S. cerevisiae*

Figure 2A:
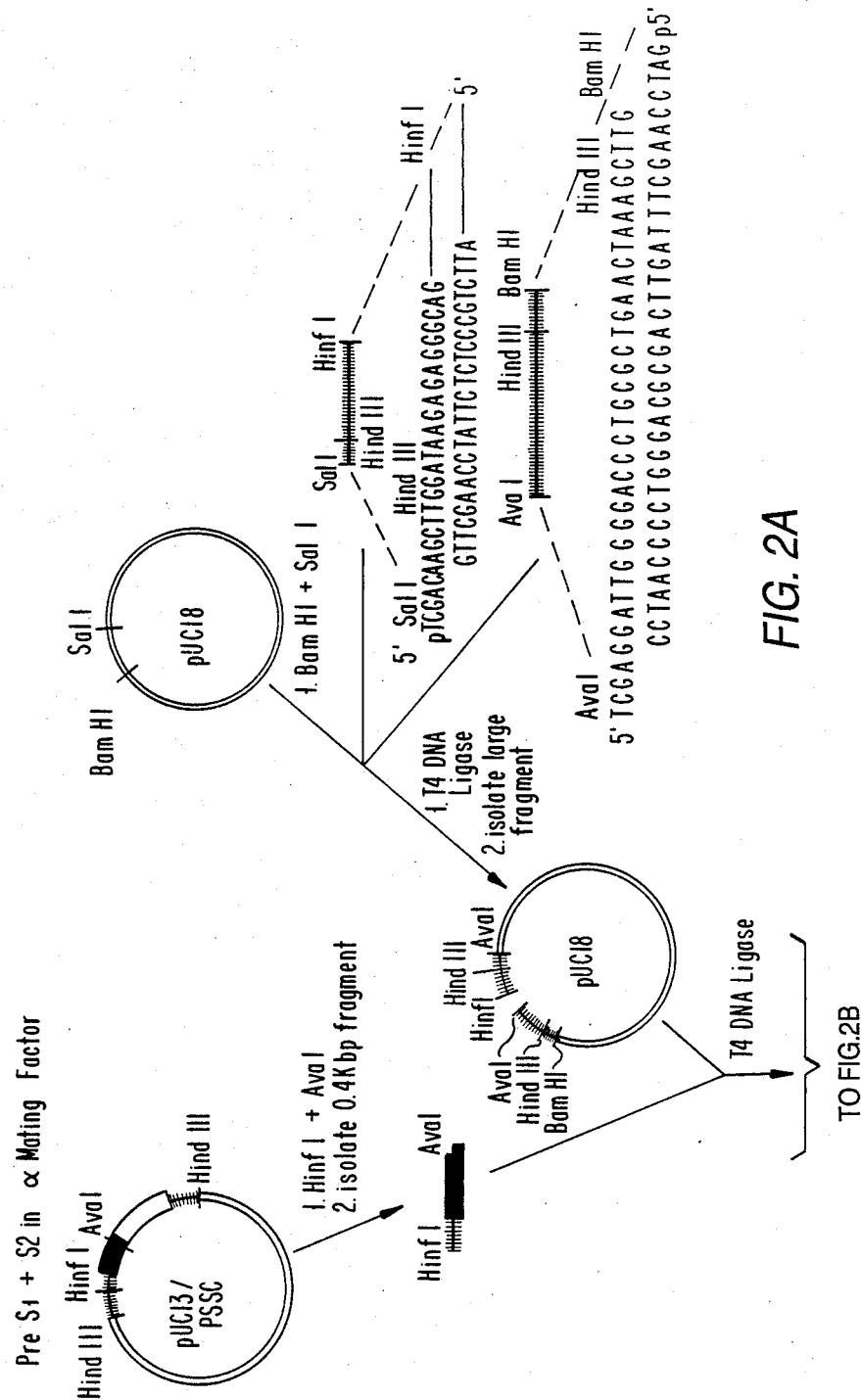
FIGS. 2A and 2B are schematic diagrams illustrating the construction of plasmid pYαMF/PSΔS.
Figure 2B:
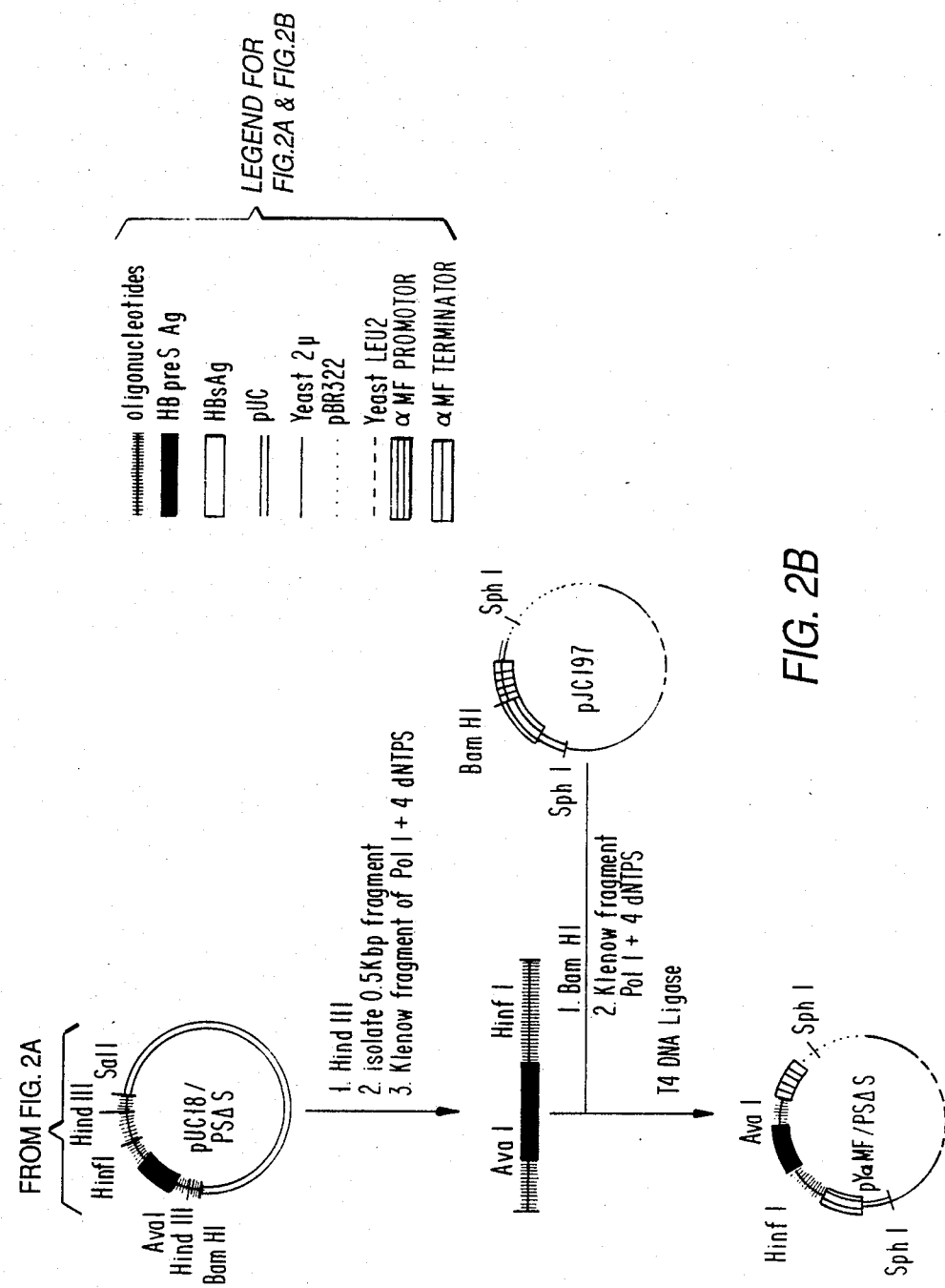

The alpha mating factor gene MFα1 had been cloned onto a plasmid vector from *S. cerevisiae* genomic DNA [Kurjan et al., Cell 30: 933 (1982); Singh et al., Nucleic Acids Res. 11: 4049 (1983)]. The resulting plasmid pKH2 was digested with EcoRI and the 1.7 kbp fragment bearing the alpha mating factor gene was purified by preparative agarose gel electrophoresis. Plasmid pRJ148 (a modified pBR322 lacking the HindIII site) was digested with EcoRI and ligated with the 1.7 kbp fragment to yield the plasmid pRJ159. This DNA was digested with HindIII and self-ligated to form plasmid pRJ167, which now has a unique HindIII site. Plasmid pRJ167 was digested with HindIII and modified by the insertion of a synthetic oligonucleotide adaptor to yield a new plasmid (pRJ178) containing a unique HindIII site which is to the 3′ side of the promoter and pre-pro-leader and to the 5′ side of the translational termination signals in all three reading frames (FIG. 2). The HindIII site was converted to a BamHI site by digestion with HindIII, flush-ending with the Klenow fragment of DNA polymerase I, addition of BamHI linkers and self-ligation to form plasmid pJC193. This plasmid was digested with EcoRI, flush-ended with the Klenow fragment of DNA polymerase I, modified by the addition of BclI linkers, digested with BclI, and the 1.5 kbp fragment bearing the alpha mating factor gene isolated by preparative gel electrophoresis. This resulting BclI fragment was treated with calf intestine alkaline phosphatase and was inserted into the unique BamHI site of pCl/1, destroying the original BamHI site in the process (plasmid pJC194). This DNA was digested with BamHI and self-ligated to remove excess BamHI linkers, resulting in the new alpha mating factor expression plasmid pJC197 (FIG. 3). The pUC13/PSSC plasmid (described in Example 1) was digested with HinfI and AvaI, and the 0.45 kbp ORF was purified by preparative agarose gel electrophoresis (FIG. 4). pUC18 was digested with SalI and BamHI, then ligated to 2 synthetic oligonucleotides. The 5' oligonucleotide consists of a SalI terminus, a HindIII site, nucleotides encoding a KEX2 cleavage site, nucleotides encoding amino acids 2 and 3 of preS-1, and a HinfI end. The structure of this oligonucleotide is

TCGACAAGCTTGGATAAGAGAGGGCAG
GTTCGAACCTATTCTCTCCCGTCTTA

The 3' oligonucleotide contains an AvaI site, nucleotides encoding the final 8 amino acids of preS-2, the stop codon, a HindIII site, and a BamHI end. The structure of this oligonucleotide is

TCGAGGATTGGGGACCCTGCGCTGAAC-
TAAAGCTTG
CCTAACCCCTGGGACGCGACTTGATTT-
CGAACCTAG

The 0.5 kbp ORF was cloned into this oligonucleotide-linkered pUC18 vector (FIG. 4). The resulting vector was digested with HindIII and blunt-ended with the Klenow fragment of DNA polymerase I. The 0.5 kbp preS-1/ (pydMF/PS S FIG. 4) resulting in the preS1/-preS2 ORF operably linked to the alpha factor pre-pro-leader. preS-2 ORF was purified by preparative agarose gel electrophoresis and cloned into pJC197 which had been digested with BamHI and blunt-ended with the Klenow fragment of DNA polymerase 1 (pYαMF/PSΔS, FIG. 4), resulting in the preS1/preS2 ORF operably linked to the alpha factor pre-pro-leader.

The alpha mating factor promoter is active only in cells which are phenotypically α [Brake et al., Mol. Cell Biol. 3: 1440 (1983)]. There are 4 loci in *S. cerevisiae*, known as SIR, which synthesize proteins required for the repression of other normally silent copies of a and α information [Rine et al., Genetics 93: 877 (1979)]. Strain JRY188 cells (MATα, sir3-8, leu2-3, leu2-112, trp1, ura3-52, his4) contain a temperature-sensitive lesion in the SIR3 gene product. As a result, JRY188 cells grown at 35° C. are phenotypically a/α and the alpha mating factor promoter is not active; on the other hand, cells grown at 23° C. are phenotypically α and thus capable of inducing an expression directed by the alpha mating factor promoter [Brake et al., Proc. Natl. Acad. Sci. U.S.A. 81: 4642 (1984)]. The recombinant preS-1/preS-2-containing alpha mating factor plasmid was used to transform *S. cerevisiae* strain JRY188 and transformed clones were selected. Cells were grown in synthetic selective (leu-) medium at 37° C.; subsequently, cells at $A^{600}=0.5$ were grown in the same medium at 23° C. Lysates were prepared, resolved by SDS-PAGE, and Western blotted to nitrocellulose. A p21 product was found to be specific to preS-1/preS-2 by virtue of its presence only in transformants and its reactivity with convalescent human HB sera.

EXAMPLE 6

Purification of preS-1/preS-2/S in particulate form by means of immune affinity chromatography Recombinant *S. cerevisiae*, constructed as described in Example 3 (complete preS sequence including amino acids 2-15), were grown in a 16 liter New Brunswick Scientific fermenter charged with 9.0 liters of synthetic selective glycerol-lactic acid medium, composed as described in Example 3. Fermentation conditions were 250 rpm agitation, 2.5 liters air/minute at 30° C. After growth to $A^{660}=0.25$, product synthesis was induced by the addition of galactose [2% (w/v)] and fermentation was continued for an additional 33 hours to a final $A^{660}=2.40$. The yeast cells were harvested by microfiltration in an Amicon DC-10 unit, suspended in 30 ml buffer A [0.1M Na$_2$HPO$_4$, pH 7.2, 0.5M NaCl], and broken in a Stansted pressure cell for seven passages at 75-85 pounds per square inch. The broken cell suspension (31 gm wet cell wes was diluted with 120 ml buffer A, Triton X100 ® was added to a final concentration of 0.5% (w/v), and the suspension was clarified by centrifugation at 10,000×g for 20 min. at 4° C. The clarified broth was decanted and incubated with Sepharose 4B coupled with antibodies to HBsAg [McAleer et al., Nature 307: 178 (1984)] for 19 hours at 4° C. to adsorb the antigen onto the resin. After the incubation period, the slurry was warmed to room temperature for all subsequent steps and degassed under vacuum for 15 min. The degassed slurry was poured into a 2.5×40 cm column. When the column had been packed fully, unbound protein was washed away with buffer A. The antigen was eluted with 3M KSCN in buffer A. Fractions containing antigen were dialyzed against 0.007M Na$_2$HPO$_4$, pH 7.2, 0.15M NaCl at 4° C. and pooled to form the Dialyzed Affinity Pool containing 1.08 mg of protein in 20 ml. Sixteen ml of Dialyzed Affinity Pool was diluted to 40 mcg/ml with 5.6 ml 0.006M Na$_2$HPO$_4$, pH 7.2, 0.15M NaCl. The product was sterilized by filtration through a Millex-GV 0.22 μm membrane. The identity of the product in the Dialyzed Affinity Pool was verified by the detection of HBsAg by Ausria ® reactivity and polymerized human albumin binding activity.

EXAMPLE 7

Purification of preS-1/preS-2/S in Particulate Form by Means of Immune Affinity Chromatography Recombinant *S. cerevisiae*, constructed as described in Example 4 (complete preS sequence including amino acids 2-15), were grown in a 16 liter New Brunswick Scientific fermenter charged with 9.0 liters of complex medium, made as described (YPD in *Methods in Yeast Genetics* p. 61, Cold Spring Harbor Laboratory, Cold Spring Harbor, N.Y.), except that HySoy (amber) was substituted for peptone. Fermentation conditions were 500 rpm agitation, 5.0 liters air/minute at 30° C. for 44 hours from $A^{600}=0.65$ to $A^{600}=9.50$. The yeast cells were harvested and lysed, and the preS-1/preS-2/S product purified as described in Example 6. The identity of the product was verified by the detection of HBsAg by Ausria ® reactivity, polymerized human albumin binding activity, and the presence of p39 in Western blots which were developed using convalescent human serum and radiolabelled *Staphylococcus aureus* Protein A.

What is claimed is:

1. An immunogenic HBV polypeptide comprising all of the preS-1 peptide and all of the preS-2 peptide, said polypeptide being free of other HBV peptides.

2. An HBV polypeptide according to claim 1 additionally containing all of the S peptide, said peptide being free of other HBV peptides.

3. An HBV polypeptide according to claim 2 that lacks amino acids 2-15 of the preS-1 region.

* * * * *